United States Patent
Crivelli et al.

(10) Patent No.: US 8,285,386 B2
(45) Date of Patent: Oct. 9, 2012

(54) IMPLANT REVISION RECOGNITION BY EXCHANGING THE REVISION DATA DURING TRANSMISSION

(75) Inventors: Rocco Crivelli, Bellinzona (CH); Alec Ginggen, Plymouth, MA (US)

(73) Assignee: Codman Neuro Sciences Sárl, Le Locle (CH)

( * ) Notice: Subject to any disclaimer, the term of this patent is extended or adjusted under 35 U.S.C. 154(b) by 1044 days.

(21) Appl. No.: 12/070,618

(22) Filed: Feb. 19, 2008

(65) Prior Publication Data

US 2009/0210033 A1 Aug. 20, 2009

(51) Int. Cl.
*A61N 1/08* (2006.01)

(52) U.S. Cl. .................. 607/59; 607/2; 607/60
(58) Field of Classification Search ............ 607/32, 607/59, 60, 2, 30, 31
See application file for complete search history.

(56) References Cited

U.S. PATENT DOCUMENTS

| | | | |
|---|---|---|---|
| 4,049,004 A | 9/1977 | Walters | |
| 5,800,473 A | 9/1998 | Faisandier | |
| 5,885,245 A | 3/1999 | Lynch et al. | |
| 6,073,049 A | 6/2000 | Alt et al. | |
| 6,480,745 B2 * | 11/2002 | Nelson et al. | 607/60 |
| 6,512,954 B2 | 1/2003 | Fox et al. | |
| 6,687,546 B2 | 2/2004 | Lebel et al. | |
| 6,689,091 B2 | 2/2004 | Bui et al. | |
| 6,758,810 B2 | 7/2004 | Lebel et al. | |
| 6,768,425 B2 | 7/2004 | Flaherty et al. | |
| 6,792,311 B2 | 9/2004 | Fox et al. | |
| 6,811,533 B2 | 11/2004 | Lebel et al. | |
| 7,069,552 B2 | 6/2006 | Lindberg et al. | |
| 7,110,823 B2 | 9/2006 | Whitehurst et al. | |
| 2002/0026122 A1 * | 2/2002 | Lee et al. | 600/523 |
| 2003/0187484 A1 * | 10/2003 | Davis et al. | 607/60 |
| 2004/0024429 A1 | 2/2004 | Daly | |
| 2004/0049246 A1 * | 3/2004 | Almendinger et al. | 607/60 |
| 2004/0260363 A1 | 12/2004 | Arx et al. | |
| 2005/0240246 A1 | 10/2005 | Lee et al. | |
| 2006/0167496 A1 * | 7/2006 | Nelson et al. | 607/2 |
| 2007/0250130 A1 * | 10/2007 | Ball et al. | 607/32 |

FOREIGN PATENT DOCUMENTS

| WO | WO 00/70889 | 11/2000 |
|---|---|---|
| WO | WO 01/47597 | 7/2001 |

* cited by examiner

*Primary Examiner* — Carl H Layno
*Assistant Examiner* — Pamela M Bays
(74) *Attorney, Agent, or Firm* — Cheryl F. Cohen, LLC

(57) ABSTRACT

A system and method for establishing communication among a control device and an implantable medical device. The implantable medical device transmits to the control device identification information including a unique identification number associated with the implantable medical device and/or a current version of application software currently being utilized by the implantable medical device. Based on the extracted identification information, the control device correlates thereto a version of the application software from among the multiple versions of application software associated with the control device that is compatible with the recognized version of the application software currently being utilized by the implantable medical device.

16 Claims, 2 Drawing Sheets

IMPLANT REVISION RECOGNITION BY EXCHANGING THE REVISION DATA DURING TRANSMISSION

BACKGROUND OF THE INVENTION

1. Field of the Invention

The present invention is directed to insuring the use of compatible versions of updated application software by both an implantable medical device and a control device by which the implant is programmed.

2. Description of Related Art

Application software instrumental in operating an electronic device may be upgraded thereby producing different versions or generations. These upgrades or different versions may provide additional features and/or correct for programming errors. Today it is not uncommon for electronic devices to communicate with one another. To insure proper operation among the devices it is important that the version of application or operating software associated with each device be compatible.

One specific example is in the case of an implantable medical device whose operation is programmed via a control device, typically an external wireless control device disposed outside the body. Over a period of time, multiple versions of application software may be installed in different implantable medical devices. It is therefore essential that the application software for operating a control device be compatible with the current version of the application software utilized by the implantable medical device being programmed using that control device.

Some concerns and problems associated with the use of different versions of application software in an implantable medical device have been addressed. U.S. Pat. No. 5,800,473 discloses a system and method for the automatic update of the software of an external programmer implant. The programmer and the implant communicate bi-directionally. Automatic updating occurs by the programmer reading the memory of the implant, establishing a list of objects that are found in the implant with their respective versions, comparing the list of the objects (and their versions) that are in the programmer software, downloading from the implant those objects which are not found in the programmer software; and/or downloading from the implant those objects in the programmer software whose version is prior to the version of the object found in the implant, and to replace the programmer software objects, with the more current version. This patented approach, however, is disadvantageous in that since the current version replaces the previous programmer software objects, only one version of the software is stored in the programmer at any given time thereby requiring that the current version of the programming software be downloaded from the implant to the programmer.

Additional disadvantages associated with the patented system include: (a) significant hardware and software complexity required on the implant side; (b) energy transfer; (c) lifetime, and (d) communication time. Each of these issues will be addressed separately.

With respect to the issue of the complexity of the implant software, since the implant application software is wirelessly upgradeable, the implant requires independent software (e.g., boot loader software) separate from the application software to manage the upgrade process of the application software. The management of the programming process insured by this separate software significantly effects both the software and hardware complexity of the implant implementation. In a first aspect, this separate programming managing software has to insure that some of the implant functionalities remain active while the application software is being updated (during the period in which the programming is downloaded the application software cannot be active, and, yet certain functionality associated with the implant must remain active, e.g., a pacemaker must monitor the pace at all times). Second, this separate programming managing software has to insure the programming process is safe and performs without errors (the error management and the verification of the integrity of the new updated code requires relatively complex software).

The next disadvantages to be addressed are that of energy transfer and lifetime. During programming, any non-volatile flash memory typically requires a larger supply voltage to operate and thus a level of energy considerably higher than the level required for a non-programmable read only memory device. This can be a disadvantage with respect to both active (with battery) and passive (without battery) implants. In the case of active implants, the lifetime of the implant may be significantly affected, whereas in the case of passive implants, it is difficult to transfer a sufficient amount of energy to the implant because of technical reasons and/or regulatory limitations, for example, specific absorption rate.

The last disadvantage associated with the patented system is that of communication time. Depending on the size of the code to be updated and on the wireless data rate, the communication time can be significantly impacted.

It is therefore desirable to store all possible versions, or at least multiple versions, of the application software in the control device compatible with all existing versions, or at least multiple versions, of the implantable medical device application software thereby eliminating having to download application programming updates from the implant to the control device while still insuring that the control device correlates a compatible version of its application software with the current application software being utilized by any particular implantable medical device.

SUMMARY OF THE INVENTION

One aspect of the present invention is directed to a method for establishing communication among a control device having a first memory device for storing multiple versions of application software for operation of the control device and an implantable medical device having a second memory device for storing a single current version of the application software for operation of the implantable medical device. An interrogation signal is generated by the control device and transmitted to the implantable medical device with which it is in communication. At the implantable medical device a response signal is generated including identification information associated with the implantable medical device and transmitted back to the control device with which it is in communication. The identification information is extracted from the response signal received by the control device, the identification information including at least one of a unique identification number associated with the implantable medical device and a current version of application software currently being utilized by the implantable medical device. Based on the extracted identification information associated with the implantable medical device, the control device correlates thereto a version of the application software from among the multiple versions of application software associated with the control device that is compatible with the recognized version of the application software currently being utilized by the implantable medical device.

Another aspect of the invention is directed to a communication system including a control device having a first memory device for storing multiple versions of application software for operation of the control device and a first processor for generating an interrogation signal. The communication system further includes an implantable medical device in communication with the control device. The implantable medical device has a second memory device for storing a single current version of the application software for operation of the implantable medical device; and a second processor for generating at the implantable medical device a response signal including identification information associated with the implantable medical device in response to the interrogation signal generated by the first processor. The first processor extracts the identification information from the response signal received by the control device, wherein the identification information includes at least one of a unique identification number associated with the implantable medical device and a current version of application software currently being utilized by the implantable medical device; and based on the extracted identification information associated with the implantable medical device, the first processor correlates thereto a version of the application software from among the multiple versions of application software associated with the control device that is compatible with the recognized version of the application software currently being utilized by the implantable medical device.

BRIEF DESCRIPTION OF THE DRAWING

The foregoing and other features of the present invention will be more readily apparent from the following detailed description and drawings of illustrative embodiments of the invention wherein like reference numbers refer to similar elements throughout the several views and in which.

DETAILED DESCRIPTION OF THE INVENTION

Figure 1:
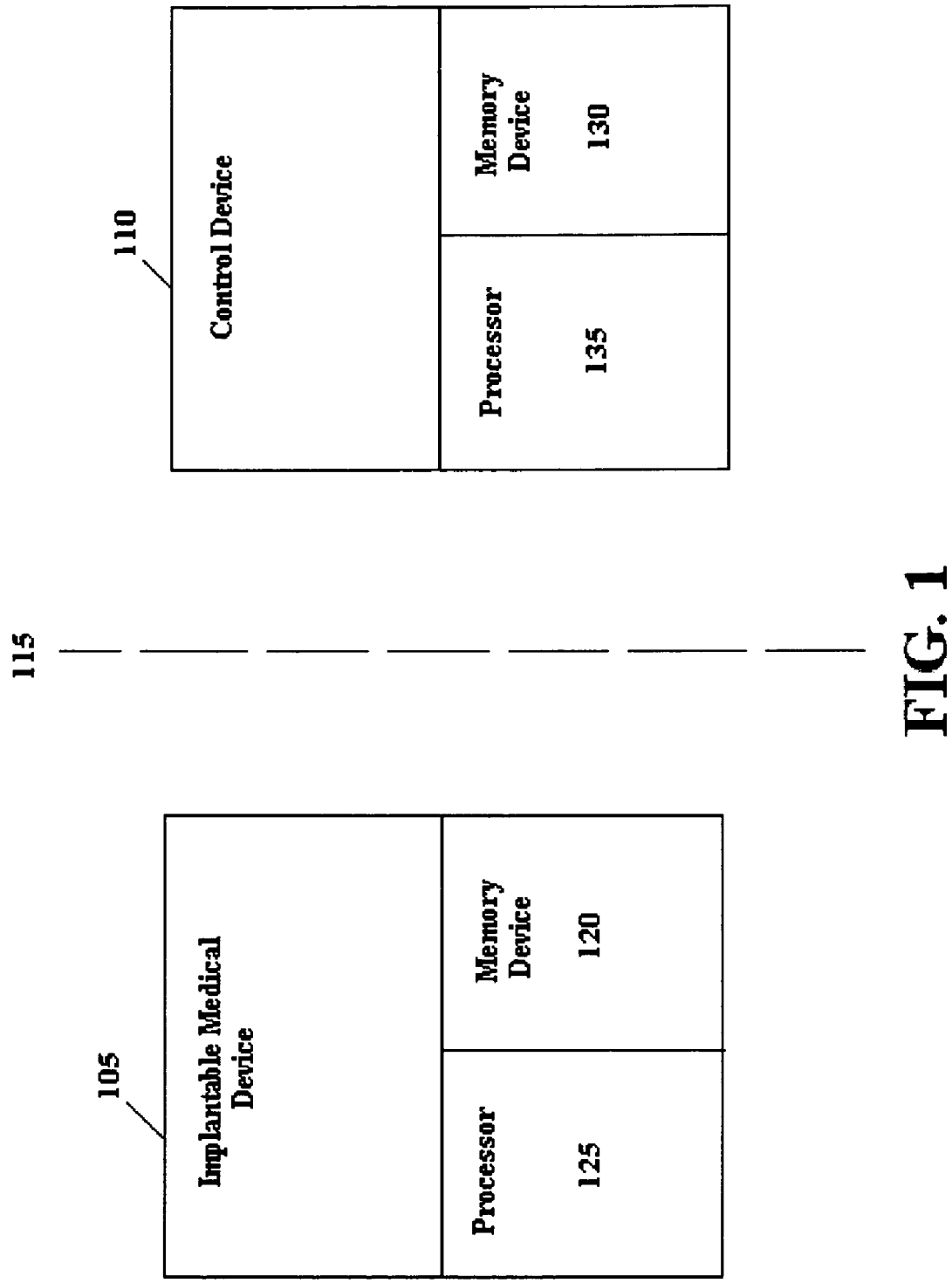
FIG. 1 is an exemplary schematic diagram of an implantable medical device wirelessly programmed via an external control device.

FIG. 1 is an exemplary schematic diagram of an implantable medical device 105 such as a drug infusion pump, cardiac pacemaker, defibrillator, cardioverter, cochlear implant, electrical stimulator or biological collector. Implantable medical device 105 has a memory device 120 and a processor 125 for storing and executing a single current version of the application software that controls its operation. Memory device 120 is shown to be included as part of the implantable medical device 105, however, the memory device 120 may alternatively be separate or remote from, but nevertheless accessible by, the implantable medical device 105. The current version of the application software stored in memory device 120 of the implantable medical device 105 may be updated by being replaced with a new version of the application software. Alternatively, instead of merely updating the application software the implantable medical device 105 itself may be replaced with another device having an updated version of the application software. Implantable medical device 105 is separated by a boundary 115 (e.g., skin) from and programmed by a control device 110, preferably via wireless communication. Despite the fact that the control device 110 shown in FIG. 1 is disposed external to the body, the control device may alternatively be implanted as well.

Control device 110 has a processor 135 and a memory device 130 for storing multiple versions, preferably all possible updates, versions or generations of the application software for controlling its operation. Memory device 130 is shown to be included as part of the control device 110, however, the memory device 130 may alternatively be separate or remote from, but nevertheless accessible by, the control device 110. It is contemplated that all possible updates, versions or generations of the application software for programming its operation may be stored in the memory device 103 of the control device 110. However, if a particular version of the application software for the implantable medical device 105 has been recalled, then its compatible version of application software for operation of the control device 110 need not necessarily be retained in the memory device 130 for safety reasons thereby optimizing available memory capacity. Other reasons for storing more than one, but less than all, possible updates or generations of the application software are also recognized. Each new update, version or generation of the application software for the control device 110 is stored in memory device 130 without replacing any prior generations or versions. Storing multiple, preferably all, updates, versions and generations of the application software for the control device in memory device 130 permits a single control device to communicate among multiple implantable devices operating using different versions of the application software without having to download application software from an implantable medical device 105 to the control device 110, as heretofore performed.

Since multiple versions of the application software for the control device 110 may be simultaneously stored in memory device 130 at any given time some versions of the stored application software for the control device may be incompatible with the particular version of application software currently utilized an implantable medical device 105. Processor 135 is instrumental in selecting a compatible application software for operating the control device 110 from among the different versions of application software stored in memory device 130 based on the recognized version of application software currently utilized by the implantable medical device 105.

To establish communication, control device 110 transmits an interrogation signal to the implantable medical device 105. In turn, the implantable medical device 105 generates and transmits a response signal back to the control device 110. Embedded within or associated with the response signal is identification information associated with the implantable medical device 105. The identification information associated with the implantable medical device 105 may be inserted anywhere in the message or telegram, e.g., at the beginning, at the end, or anywhere else, thereby increasing the length of the message or telegram and its communication duration.

Alternatively, data compression techniques may be employed to mix the identification information associated with the implantable medical device with the original message or telegram without significantly effecting its length or duration of communication. A reverse algorithm may be performed on the received telegram at the control device thereby extracting the identification information that was mixed within the message or telegram.

The identification information associated with the implantable medical device 105 and transmitted to the control device 110 includes at least one of: (i) a unique identification number; and (ii) a current version of the application software by which the implantable medical device is currently operating. The unique identification number is preferably programmed in the implantable medical device 105 at the time of manufacture. If a universal or common control device 110 is used to program different products or types of implantable medical devices, the information associated with the implantable medical device 105 and transmitted to the control device 110 may include a third parameter identifying the particular product or type of implantable medical device ("Implant Device Type"). For instance, a single universal or common control device 110 may be used to program both a drug infusion delivery device and an electrical stimulator. So long as the control device 110 is used to program only a single product or type of implantable medical device, then the "Implant Device Type" parameter may be eliminated altogether.

Based on the identification information associated with the implantable medical device 105, processor 135 of control device 110 correlates or maps thereto a version of the application software for the control device that is compatible with the current version of the application software being utilized by the implantable medical device 105. Such mapping or correlation of these parameters may be realized using a look-up-table (LUT), database, other memory device or computational algorithm. An illustrative exemplary LUT in accordance with the present invention for use in control device 110 of FIG. 1 is shown in the table below.

TABLE

| Implant Device Type | Implant Software Application Version | Implant Device ID Range | Control Device Software Version | Icon Library |
|---|---|---|---|---|
| 1 | 1.00-1.03 | SN NBBBBB-SN NFBB77 | 2.02 | 2.01 |
| 1 | 1.04-1.04 | SN NFBB88-SN NFBB89 | 2.03 | 2.01 |
| 2 | 1.00-1.02 | SN NFCCCC-SN NFCC67 | 2.00 | 2.02 |
| 2 | 1.02-1.04 | SN NFCC68-SN NFCC88 | 2.01 | 2.03 |

In the exemplary LUT above, the implantable medical device 105, in response to the interrogation signal generated by the control device 110, transmits back to the control device identification information including three distinct parameters or data information, e.g., "Implant Device Type", "Implant Software Application Version" and "Implant Device ID." Each parameter will now be addressed separately. The "Implant Device Type" is a parameter that differentiates among different types of implant devices. As noted above, a common control device 110 may be used for programming different types of implantable medical devices serving different functions, such as a drug infusion delivery device and a stimulator. In such a case, the "Implant Device Type" may be used to differentiate among different types of products all programmable by a single common or universal control device 110. For instance, in the Table above, "Implant Device Type" "1" refers to an implantable drug infusion delivery device while, "Implant Device Type" "2" is assigned to an implantable stimulating device. It should be noted, that if the control device is used to program only one type of implantable medical device then this parameter may be eliminated altogether. Any number of two or more types of implantable medical devices may be differentiated by assigning them each a different "Implant Device Type" value.

In the exemplary Table, the second parameter ("Current Version of Implant Application Software") provided by the implantable medical device 105 as part of the identification information is the current version of the application software for operating the implantable medical device 105. As previously noted, typically over a period of time the operating application software for an implantable medical device is upgraded or revised. This second parameter identifies the current version of the application software being utilized by the implantable medical device by assigning it a unique value.

A third and last parameter ("Implant Identification Number") provided by the implantable medical device 105 is its unique identification number. No two implantable medical devices are assigned the same "Implant Identification Number." In the Table above, multiple predefined range values are provided, and a determination is made whether the particular "Implant Identification Number" received from the implantable medical device as part of the identification information falls within any of the predefined ranges. The illustrative example identifies each implantable medical device by a unique "Implant Identification Number" comprising a combination of letters and numbers that are assigned consecutively. As desired, the unique "Implant Identification Number" may be letters, numbers, symbols, and/or any combination thereof and need not be assigned consecutively.

Thus, in the exemplary embodiment whose parameter values are identified in the Table, the implantable medical device 105 transmits to the control device 110 its identification information including the "Implant Identification Number", the "Current Version of Implant Application Software" and the "Implant Device Type."

As previously mentioned, if the control device 110 is used to control only a single type of implant device 105 then the identification information may be reduced to include only two parameters ("Implant Identification Number" and "Current Version of Implant Application Software") eliminating the parameter "Implant Device Type."

Yet another embodiment in accordance with the present invention restricts the identification information even further to include only a single parameter. For example, the identification information may only include the "Current Version of Implant Application Software." In such case, the LUT in the control device 110 maps a current version of the control device application software with the "Current Version of Implant Application Software" received from the implant as part of the identification information.

As another specific example, the identification information may include only the "Implant Identification Number." With this scenario, the LUT in the control device 110 maps the control device application software with the version compatible with the "Implant Identification Number" received from the implant as part of the identification information.

Irrespective of how many parameters are included in the identification information, two operations are performed by the control device 110 on the identification information transmitted by the implantable medical device 105. The first operation is to determine whether the implantable medical device 105 is compatible with the control device 110. This operation is performed by determining whether the identification information satisfies all the criteria for a particular row in the LUT. In the illustrative example shown in the Table above, this operation is performed by determining whether the identification information (e.g., "Implant Device Type", "Current Version of Implant Application Software" and "Implant Identification Number") fall within the parameter ranges of a particular row of the LUT. A logical AND operation is preferably used to perform this function. If the result of the logical AND operation is "0", then the implantable medical device 105 is not compatible with the control device 110 and communication ceases. If desired, an audible and/or visual indication device may be activated to alert the user of the incompatibility among the two devices. Otherwise, if the result of the logical AND operation is a "1", then the implantable medical device 105 is compatible with the control device 110 and a second operation is performed. In particular, this second operation is the selection of the application software for the control device 110 that is compatible with the current version of the application software being utilized by the implantable medical device 105. This selection of the compatible application software for the control device 110 is based on the identification information provided by the implantable medical device 105.

The last entry in the Table above is identified as "Icon Library." Based on the compatible application software for the control device 110 obtained from the LUT, associated icon libraries for the graphic user interface may be displayed on the control device 110.

Accordingly, whenever the application software of the implantable medical device 105 is updated, the information in the LUT is also updated to conform with one another. In addition, the LUT is also updated to store therein all versions of the control device application software that may be compatible with any of the versions of the application software for an implantable medical device.

All operations of the control device 110 thereafter utilize the compatible application software for the control device as determined from the LUT. The present inventive system and method thus insures that the operation of the control device utilizes a version of its application software that is compatible with the current version installed in the implantable medical device.

A control device 110 in accordance with the present invention is therefore able to operate with implantable medical devices regardless of the current version or generation of programming software installed therein. Memory device 130 of control device 110 may store more than one version of the control device programming software, preferably all generations of the control device programming software. At least one version of the control device application software stored in memory device 130 is compatible with a corresponding version of the application software currently utilized by an implantable medical device 105 in which the control device is in communication. This relationship may be a one-to-one relationship whereby for each version of the implantable medical device application software there is one, and only one, compatible version of the control device application software. Relationships, other than a one-to-one relationship between the implantable medical device application software and the compatible version of the control device application software may alternatively be used, as desired. For instance, if there are two generations of application software for the implantable medical device and a single version of the application software for the control device, the only version of the application software for the control device may be compatible with either the first version (earlier version) or the second version (later version) of the application software for the implantable medical device. Such may be the case, when the updated version of the implantable medical device application software merely corrects for programming errors without changing the features. Therefore, there may be no need to update the version of the control device application software assuming it also does not experience any programming errors that need to be corrected.

The exemplary embodiment shown in FIG. 1 and described in the preceding paragraphs is but one specific application and not intended to limit in any way the scope of the present invention. Accordingly, the invention is not limited in scope to a medical application or use, nor to an implantable medical device and associated control device. Instead, the present invention may be utilized by any two electronic devices in wireless communication with one another.

Figure 2:
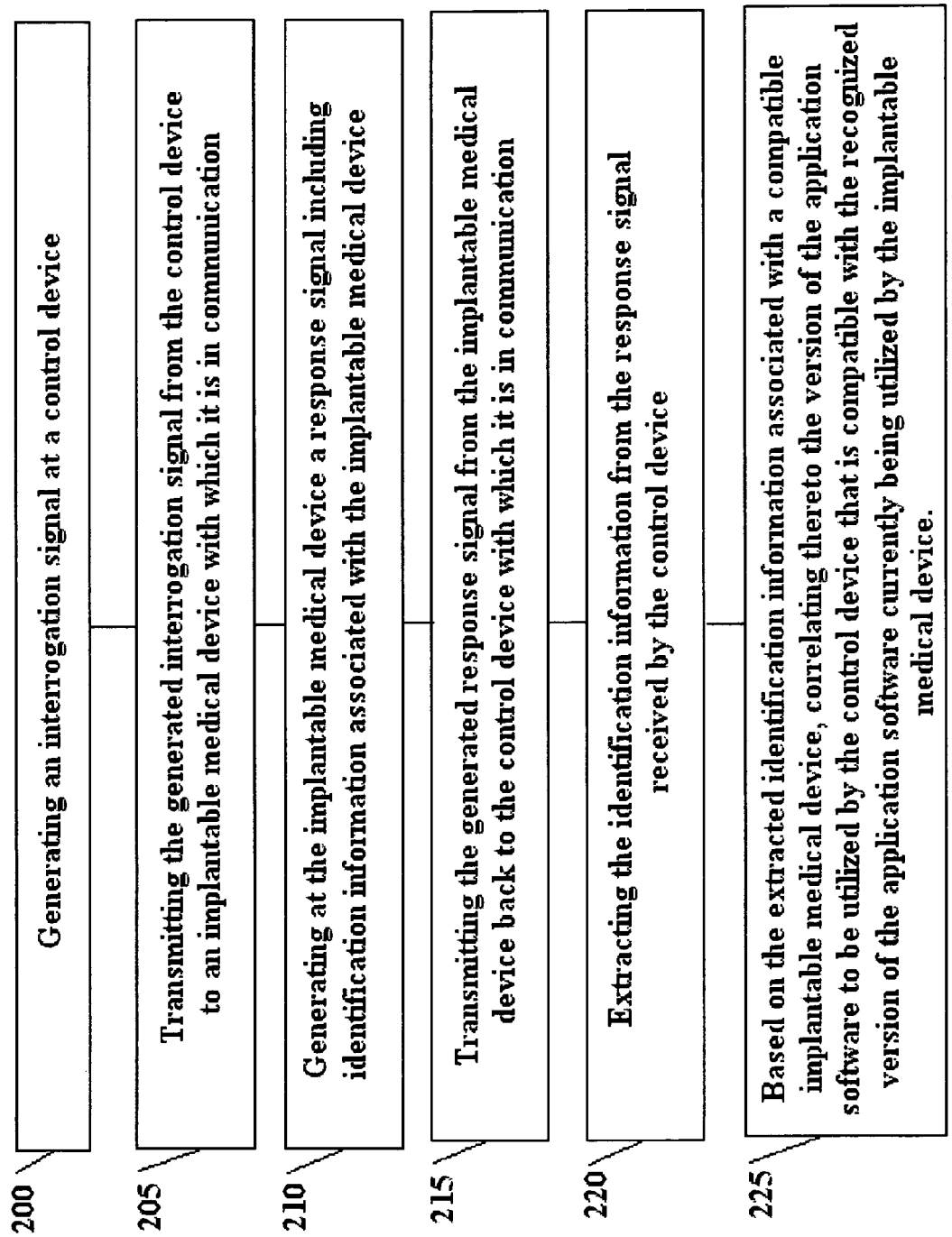
FIG. 2 is a flow chart of the method for recognition and selection of compatible versions of application software among two electronic devices in communication with one another in accordance with the present invention.

FIG. 2 is an exemplary flow chart in accordance with the present invention of the method for recognition and selection of compatible versions of application software among a control device and an implantable medical device in wireless communication with one another. An interrogation signal is generated by the control device in step 200 and thereafter transmitted in step 205 from the control device to the implantable medical device with which it is in wireless communication. In step 210, the implantable medical device, in turn, generates a response signal that includes identification information associated with the implantable medical device. The generated response signal is transmitted in step 215 from the implantable medical device back to the control device. Upon receipt of the response signal, in step 220 the control device extracts the identification information (including at least one of the "Implant Identification Number" and the "Current Version of Implant Application Software") from the response signal. Confirmation is made that the two devices are compatible with one another, for example, by ascertaining whether the extracted identification information corresponds with an entry in a LUT. Based on the identification information associated with a compatible implantable medical device, a LUT or analogous device associated with the control device is then used in step 225 to correlate or map thereto the version of application software to be utilized by the control device that is compatible with the recognized version of application software currently being utilized by the implantable medical device.

The present inventive system and method therefore insures that the control and implantable medical devices utilize compatible application software while circumventing having to download current application software between the two devices.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. Method for establishing communication among a control device having a first memory device for storing multiple versions of application software for operation of the control device and an implantable medical device having a second memory device for storing single current version of the application software for operation of the implantable medical device, comprising the steps of:

generating an interrogation signal at the control device;

transmitting the generated interrogation signal from the control device to the implantable medical device with which it is in communication;

generating at the implantable medical device a response signal including identification information associated with the implantable medical device;

transmitting the generated response signal from the implantable medical device back to the control device with which it is in communication;

extracting the identification information from the response signal received by the control device, the identification information including both a unique identification number associated with the implantable medical device and a current version of application software currently being utilized by the implantable medical device; and based on the extracted identification information associated with the implantable medical device, correlating thereto a version of the application software from among the multiple versions of application software associated with the control device that is compatible with the recognized version of the application software currently being utilized by the implantable medical device.

2. The method in accordance with claim 1, wherein the correlating step utilizes a look-up-table.

3. The method in accordance with claim 1, wherein the correlating step utilizes an algorithm.

4. The method in accordance with claim 1, wherein the identification information is added onto the response signal thereby increasing its overall length.

5. The method in accordance with claim 1, wherein the identification information is mixed with the response signal using an encoding scheme without increasing its overall length.

6. The method in accordance with claim 1, wherein the identification information further includes information concerning the type of implant.

7. The method in accordance with claim 1, wherein the first memory device stores all possible versions of the application software for the control device.

8. The method in accordance with claim 1, wherein the compatible application software for the control device is utilized without having to transmit application software between the two devices.

9. A communication system comprising:
a control device comprising:
a first memory device for storing multiple versions of application software for operation of the control device;
a first processor for generating an interrogation signal;
an implantable medical device in communication with the control device, the implantable medical device comprising:
a second memory device for storing a single current version of the application software for operation of the implantable medical device;
a second processor for generating at the implantable medical device a response signal including identification information associated with the implantable medical device in response to the interrogation signal generated by the first processor;
wherein the first processor extracts the identification information from the response signal received by the control device, the identification information including both a unique identification number associated with the implantable medical device and a current version of application software currently being utilized by the implantable medical device; and based on the extracted identification information associated with the implantable medical device, the first processor correlates thereto a version of the application software from among the multiple versions of application software associated with the control device that is compatible with the recognized version of the application software currently being utilized by the implantable medical device.

10. The system in accordance with claim 9, wherein the first processor further comprises a look-up-table for correlating the version of the application software from among the multiple versions of application software associated with the control device that is compatible with the recognized version of the application software currently being utilized by the implantable medical device.

11. The system in accordance with claim 9, wherein the first processor uses an algorithm for correlating the version of the application software from among the multiple versions of application software associated with the control device that is compatible with the recognized version of the application software currently being utilized by the implantable medical device.

12. The system in accordance with claim 9, wherein the identification information is added onto the response signal thereby increasing its overall length.

13. The system in accordance with claim 9, wherein the identification information is mixed with the response signal using an encoding scheme without increasing its overall length.

14. The system in accordance with claim 9, wherein the identification information includes information concerning the type of implant.

15. The system in accordance with claim 9, wherein the first memory device stores all possible versions of the application software for the control device.

16. The system in accordance with claim 9, wherein the compatible application software for the control device is utilized without having to transmit application software between the two devices.

* * * * *